United States Patent [19]

Kuchikata et al.

[11] 4,315,846

[45] Feb. 16, 1982

[54] METAL SALT OF N-SUBSTITUTED ALKYLENEBISDITHIOCARBAMIC ACID

[75] Inventors: Masuo Kuchikata; Hiroshi Tsuyuki, both of Urawa; Toshio Furukawa, Tokyo; Yoshihiro Nitta, Komae; Hiroshi Kuyama, Urawa, all of Japan

[73] Assignee: Tokyo Organic Chemical Industries, Ltd., Tokyo, Japan

[21] Appl. No.: 133,994

[22] Filed: Mar. 26, 1980

[51] Int. Cl.$^3$ ............................................... C07F 3/06
[52] U.S. Cl. ............................ 260/429.9; 260/429 K; 260/429.7; 260/438.1; 260/439 R; 562/557
[58] Field of Search ........................ 260/429 K, 429.9; 424/286; 562/557

[56] References Cited

U.S. PATENT DOCUMENTS

| | | | |
|---|---|---|---|
| 1,610,216 | 12/1926 | Elley | 260/429 K |
| 2,342,232 | 2/1944 | Dean | 260/429 K |
| 2,733,262 | 1/1956 | Brittan et al. | 260/429.9 X |
| 3,294,829 | 12/1966 | Lehmann et al. | 260/429 K |
| 3,725,443 | 4/1973 | Horiie et al. | 260/429 K |
| 3,856,851 | 12/1974 | Buckman et al. | 260/429 K X |
| 3,880,900 | 4/1975 | Fujii et al. | 260/429 K |
| 3,973,034 | 8/1976 | Buckman et al. | 424/286 |

FOREIGN PATENT DOCUMENTS 2359124 2/1978 France.

OTHER PUBLICATIONS

Thorn et al., The Dithiocarbamates and Related Compounds, Elsevier Publ. Co. N.Y. pp. 36–37 (1962).

*Primary Examiner*—Helen M. S. Sneed
*Attorney, Agent, or Firm*—Alex R. Sluzas

[57] ABSTRACT

This application relates to novel metal salts of N-substituted alkylenebisdithiocarbamic acids and their use as agricultural fungicides.

13 Claims, No Drawings

METAL SALT OF N-SUBSTITUTED ALKYLENEBISDITHIOCARBAMIC ACID

SUMMARY OF THE INVENTION

This invention relates to a metal salt of N-substituted alkylenebisdithiocarbamic acid represented by the formula:

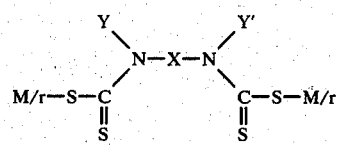

[wherein, X denotes an alipahtic chain (inclusive of both straight and branched chain), Y and Y' each denote a hydrogen atom (excluding the case wherein both Y and Y' are a hydrogen atom), a higher alkyl group,

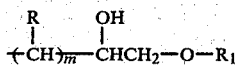

(where, R is a hydrogen atom or an alkyl group, $R_1$ is a hydrogen atom, an alkyl group, an unsaturated alkyl group, a phenyl group, or a phenyl group substituted with lower alkyl groups or one or more halogen atoms, and m is an integer having the value of 0, 1 or 2),

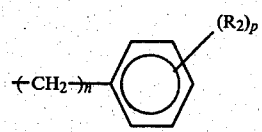

(where, $R_2$ is a hydrogen atom, an alkyl group or a halogen atom, n is an integer having the value of 1 or 2 and p is an integer having the value of 0, 1, 2 or 3,

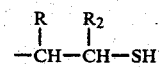

(where R and $R_2$ are the same as described above),

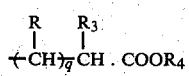

(R is the same as described above, $R_3$ is a hydrogen atom, a lower alkyl group or a hydroxyl group, $R_4$ is an alkyl group, a dialkylaminoalkyl group, an unsaturated alkyl group, a hydroxyalkyl group or a salt, and q is an integer having the value of 0 or 1),

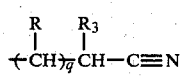

(where, R, $R_3$ and q are the same as described above),

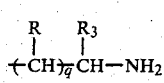

(where R, $R_3$ and q are the same as described above),

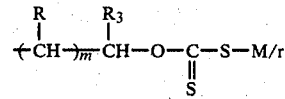

(where, R, $R_3$ and m are the same as described above, and M and r are the same as described herein below), or

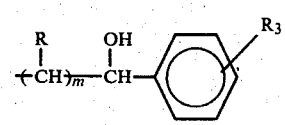

(where, R, $R_3$, and m are the same as described above), M denotes a metallic atom (not including alkali metal), and r denotes a valency], agronomically acceptable compositions containing these salts as the active ingredient and their use as agricultural fungicides.

DETAILED DESCRIPTION OF THE INVENTION

This invention relates to novel metal salts of N-substituted alkylenebisdithiocarbamic acids. These polydithiocarbamates containing substituents in place of the hydrogen atoms in the amino group as shown in the general formula (hereinafter referred to as N-substituted alkylenebisdithiocarbamates) are novel compounds and they possess fungicidal activity. Specifically, this invention relates to metal salts of N-substituted alkylenebisdithiocarbamic acids of the general formula:

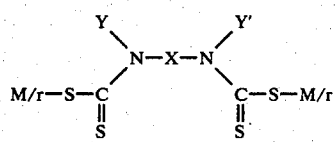

[wherein, X denotes an aliphatic chain (inclusive of both straight and branched chain), Y and Y' each denote a hydrogen atom (excluding the case wherein both Y and Y' are a hydrogen atom), a higher alkyl group,

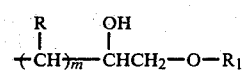

(where, R is a hydrogen atom or an alkyl group, $R_1$ is a hydrogen atom, an alkyl group, an unsaturated alkyl group, a phenyl group, or a phenyl group substituted with lower alkyl groups or one or more halogen atoms, and m is an integer having the value of 0, 1 or 2,

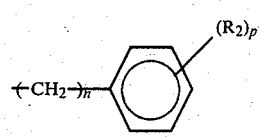

(where, $R_2$ is a hydrogen atom, an alkyl group or a halogen atom, n is an integer having the value of 1 or 2 and p is an integer having the value of 0, 1, 2 or 3),

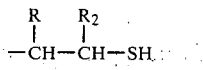

(where R and R₂ are the same as described above),

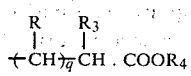

(R is the same as described above, R₃ is a hydrogen atom, a lower alkyl group or a hydroxyl group, R₄ is an alkyl group, a dialkylaminoalkyl group, an unsaturated alkyl group, a hydroxyalkyl group or a salt, and q is an integer having the value of 0 or 1),

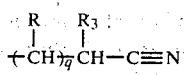

(where, R, R₃ and q are the same as described above),

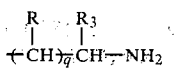

(R, R₃ and q are the same as described above),

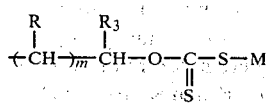

(where, R, R₃ and m are the same as described above, and M and r are the same as described herein below), or

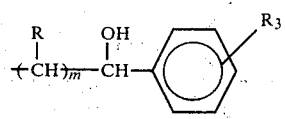

(where, R, R₃, and m are the same as described above), M denotes a metallic atom (not including alkali metal), and r denotes a valency].

The N-substituted alkylenebisdithiocarbamic acids to be used in the manufacture of the compounds of this invention are produced by the general method which utilizes to the reaction of polyamines with carbon disulfide. Examples of the polyamines to be used in this case are as follows.

N-octylethylene diamine, N-nonylethylene diamine, N-(2-ethylhexyl)-ethylene diamine, N-decylethylene diamine, N-undecylethylene diamine, N-dodecylethylene diamine, N-tetradecylethylene diamine, N-cetylethylene diamine, N-octadecylethylene diamine, N-octyldiethylene triamine, N-decyldiethylene triamine, N-dodecyldiethylene triamine, N-dodecyltriethylene tetramine, N-octylpropylene diamine, N-dodecylpropylene diamine, N-octylisopropylene diamine, N-dodecylisopropylene diamine, N'-dodecylisopropylene diamine, N-dodecyl-1,1-dimethylethylene diamine, N'-dodecyl-1,1-dimethylethylene diamine, N-dodecyl-1,2-dimethylethylene diamine, N-dodecyl-1,2-diethylethylene diamine, N-(2-hydroxyethyl)-ethylene diamine, N-(2-hydroxypropyl)-ethylene diamine, N-(2-hydroxybutyl)-ethylene diamine, N-(2-hydroxy-1,2-dimethylethyl)-ethylene diamine, N-(1-hydroxyethyl)-ethylene diamine, N-(3-hydroxypropyl)ethylene diamine, N-(3-hydroxypropyl)-ethylene diamine, N-(2-hydroxyethyl)-1,3-propylene diamine, N-(2-hydroxypropyl)-1,3-propylene diamine, N-(2-hydroxyethyl)-1,2-propylene diamine, N-(2-hydroxyethyl)-2,3-propylene diamine, N-(2-hydroxypropyl)-1,2-propylene diamine, N-(2-hydroxypropyl)-2,3-propylene diamine, N-(3-hydroxypropyl)-1,2-propylene diamine, N-(3-hydroxypropyl)-2,3-propylene, the alkanol amine having one mol of ethylene oxide attached to diethylene triamine, the alkanol amine having three moles of ethylene oxide attached to diethylene triamine, the alkanol amine having one mole of ethylene oxide attached to triethylene tetramine, the alkanol amine having one mol of propylene oxide attached to diethylene triamine, the alkanol amine having two moles of propylene oxide attached to diethylene triamine, N-(2-mercaptoethyl)-ethylene diamine, N(2-mercaptoethyl)diethylene triamine, N-(2-mercaptoethyl)triethylene tetramine, N-(2-mercaptoethyl)-propylene diamine, N-(2-mercaptoethyl)isopropylene diamine, N'-(2-mercaptoethyl)-isopropylene diamine, N-(2-mercaptoethyl)-1,2-dimethylethylene diamine, N-(2-mercaptoethyl)-1,1-dimethylethylene diamine, N'-(2-mercaptoethyl)-1,1-dimethylethylene diamine, N-(2-mercaptopropyl)-ethylene diamine, N-(2-mercaptopropyl)-diethylene triamine, N-(2-mercaptopropyl)-triethylene tetramine, N-(2-mercaptopropyl)-propylene diamine, N-(2-mercaptopropyl)isopropylene diamine, N'-(2-mercaptopropyl)isopropylene diamine, N-(2-mercaptopropyl)-1,1-dimethylethylene diamine, N'-(2-mercaptopropyl)-1,1-dimethylethylene diamine, N-(3-mercaptopropyl)-ethylene diamine, N-(2-mercaptobutyl)-ethylene diamine, N-(3-mercaptopropyl)-ethylene diamine, N-(3-mercaptopropyl)-isopropylene diamine, N'-(3-mercaptopropyl)isopropylene diamine, N-(O-methylbenzyl)-ethylene diamine, N-(m-methylbenzyl)-ethylene diamine, N-(p-methylbenzyl)ethylene diamine, N-(2,3-dimethylbenzyl)-ethylene diamine, N-(2,4-dimethylbenzyl)-ethylene diamine, N-(2,5-dimethylbenzyl)-ethylene diamine, N-(3,4-dimethylbenzyl)-ethylene diamine, N-(2,4,5-trimethylbenzyl)ethylene diamine, N-(2,4,6-trimethylbenzyl)-ethylene diamine, N-(2,3,4-trimethylbenzyl)-ethylene diamine, N-(2,3,5-trimethylbenzyl)-ethylene diamine, N-(O-chlorobenzyl)-ethylene diamine, N-(m-chlorobenzyl)ethylene diamine, N-(p-chlorobenzyl)-ethylene diamine, N-(2,3-dichlorobenzyl)-ethylene diamine, N-(2,4-dichlorobenzyl)-ethylene diamine, N-(2,5-dichlorobenzyl)ethylene diamine, N-(3,4-dichlorobenzyl)-ethylene diamine, N-(3,5-dichlorobenzyl)-ethylene diamine, N-(2,4,6-trichlorobenzyl)-ethylene diamine, N-(2,4,5-trichlorobenzyl)-ethylene diamine, N-(o-bromobenzyl)ethylene diamine, N-(m-bromobenzyl)-ethylene diamine, N-(p-bromobenzyl)-ethylene diamine, N-(o-iodobenzyl)ethylene diamine, N-(m-iodobenzyl)-ethylene diamine, N-(p-iodobenzyl)-ethylene diamine, N-(p-methylbenzyl)isopropylene diamine, N'-(p-methylbenzyl)-isopropylene diamine, N-2,4-dimethylphenethyl)-ethylene diamine, N-(2,4,5-trimethylphenethyl)-ethylene diamine, N-(methoxycarbonylmethyl)-ethylene diamine, N-(ethoxycarbonylmethyl)-ethylene diamine, N-(propoxycarbonylmethyl)-ethylene diamine, N-(isopropoxycarbonylmethyl)ethylene diamine, N-(butoxycarbonylmethyl)-ethylene diamine, N-(hexyloxycarbonylmethyl)-ethylene diamine, N-(octyloxycarbonylmethyl)-ethylene diamine, N-(dodecyloxycarbonylmethyl)-ethylene diamine, N-(methoxycarbonylmethyl)-propylene diamine, N'-(methoxycarbonylmethyl)isopropylene diamine, N-(ethoxycarbonylmethyl)-isopropylene diamine, N'-(ethoxycarbonylmethyl)-ethylene diamine, N-(isopropoxycarbonylmethyl)-isopropylene diamine, N-(propoxycarbonylmethyl)-isopropylene diamine, N'-(propoxycarbonylmethyl)-isopropylene diamine, N-(butoxycarbonylmethyl)-isopropylene diamine, N'-(butoxycarbonylmethyl)-isopropylene diamine, N-(isopropoxycarbonylmethyl)-1,2-dimethylethylene diamine, N-(isopropoxydicarbonylmethyl)-1,1-dimethylethylene diamine, N'-(isopropoxycarbonylmethyl)-1,1-dimethylethylene diamine, N-(2-methoxycarbonylethyl)-ethylene diamine, N-(2-ethoxycarbonylethyl)-ethylene diamine, N-(2-isopropoxycarbonyl ethyl)-ethylene diamine, N-(2-propoxycarbonylethyl)-ethylene diamine, N-(2-butoxycarbonyl ethyl)-ethylene diamine, N-(2-hexyloxycarbonylethyl)-ethylene diamine, N-(2-octyloxycarbonylethyl)ethylene diamine, N-(2-dodecyloxycarbonylethyl)-ethylene diamine, N-(2-dodecyloxycarbonylethyl)-ethylene diamine, N-(2-tetradecyloxycarbonylethyl)-ethyl diamine, N-(2-cetyloxycarbonylethyl)-ethylene diamine, N-(2-octadecyloxycarbonylethyl)-ethylene diamine, N-(2-methoxycarbonylethyl)-propylene diamine, N-(2-ethoxycarbonylethyl)-propylene diamine, N-(2-isopropoxycarbonylethyl)propylene diamine, N-(2-isopropoxycarbonylethyl)-isopropylene diamine, N'-(2-isopropoxycarbonylethyl)-isopropylene diamine, N-(2-propoxycarbonylethyl)-isopropylene diamine, N'-(2-propoxycarbonylethyl)-isopropylene diamine, N-(2-ethoxycarbonylethyl)-isopropylene diamine, N'-(2-ethoxycarbonylethyl)-isopropylene diamine, N-(2-methoxycarbonylethyl)-isopropylene diamine, N'-(2-methoxycarbonylethyl)-isopropylene diamine, N-(2-methoxycarbonylpropyl)-ethylene diamine, N-(2-ethoxycarbonylpropyl)-ethylene diamine, N-(2-propoxycarbonylpropyl)ethylene diamine, N-(2-isopropoxycarbonylpropyl)-ethylene diamine, N-(2-butoxycarbonylpropyl)-ethylene diamine, N-(2-pentoxycarbonylpropyl)-ethylene diamine, N-(2-hexyloxycarbonylpropyl)-ethylene diamine, N-(2-octyloxycarbonylpropyl)-ethylene diamine, N-(2-decyloxycarbonylpropyl)-ethylene diamine, N-(2-dodecyloxycarbonylpropyl)-ethylene diamine, N-(2-tetradecyloxycarbonylpropyl)-ethylene diamine, N-(2-cetyloxycarbonylpropyl)-ethylene diamine, N-(2-octadecyloxycarbonylpropyl)-ethylene diamine, N-(2-methoxycarbonylpropyl)propylene diamine, N-(2-ethoxycarbonylpropyl)-propylene diamine, N-(2-propoxycarbonylpropyl)-propylene diamine, N-(2-isopropoxycarbonylpropyl)-propylene diamine, N-(2-methoxycarbonylpropyl)-isopropylene diamine, N'-(2-methoxycarbonylpropyl)-isopropylene diamine, N-(2-ethoxycarbonylpropyl)-isopropylene diamine, N'-(2-ethoxycarbonylpropyl)-isopropylene diamine, N-(2-propoxycarbonylpropyl)-isopropylene diamine, N'-(2-propoxycarbonylpropyl)-isopropylene diamine, N-(2-isopropoxycarbonylpropyl)-isopropylene diamine, N'-(2-isopropoxycarbonylpropylene)-isopropylene diamine, N-(2-butoxycarbonylpropyl)-isopropylene diamine, N'-(2-butoxycarbonylpropyl)-isopropylene diamine, N-(2-isopropoxycarbonylpropyl)-1,2-dimethylethylene diamine, N-(2-isopropoxycarbonylpropyl)-1,2-dimethylethylene diamine, N'-(2-isopropoxycarbonylpropyl)-1,1-dimethylethylene diamine, N-(2-methoxycarbonylethyl)-diethylene triamine, N-(2-ethoxycarbonylethyl)-diethyl triamine, N-(2-propoxycarbonylethyl)-diethylene triamine, N-(2-isopropoxycarbonylethyl)-diethylene triamine, N-(2-isopropoxycarbonylethyl)-triethylene tetramine, N-(2-methoxycarbonylpropyl)-diethylene triamine, N-(2-ethoxycarbonylpropyl)-diethylene triamine, N-(2-propoxycarbonylpropyl)-diethylene triamine, N-(2-isopropoxycarbonylpropyl)-diethylene triamine, N-(2-isopropoxycarbonylpropyl)-triethylene tetramine, N-(2,3-dihydroxypropyl)-ethylene diamine, N-(2,3-dihydroxypropyl)propylene diamine, N-(2-dihydroxypropyl)isopropylene diamine, N'-(2,3-dihydroxypropyl)-isopropylene diamine, N-(2,3-dihydroxypropyl)-diethylene triamine, N-(2,3-dihydroxypropyl)-triethylene tetramine, N-(2,3-dihydroxypropyl)-1,2-dimethylethylene diamine, N-(2-hydroxy-3-methoxypropyl)-ethylene diamine, N-(2-hydroxy-3-methoxypropyl)-propylene diamine, N-(2-hydroxy-3-methoxypropyl)-isopropylene diamine, N'-(2-hydroxy-3-methoxypropyl)-isopropylene diamine, N-(2-hydroxy-3-methoxypropyl)-1,2-dimethylethylene diamine, N-(2-hydroxy-3-ethoxypropyl)-ethylene diamine, N-(2-hydroxy-3-ethoxypropyl)-propylene diamine, N-(2-hydroxy-3-ethoxypropyl)isopropylene diamine, N'-(2-hydroxy-3-ethoxypropyl)isopropylene diamine, N-(2-hydroxy-3-ethoxypropyl)diethylene triamine, N-(2-hydroxy-3-ethoxypropyl)-triethylene tetramine, N-(2-hydroxy-3-ethoxypropyl)-1,2-dimethylethylene diamine, N-(2-hydroxy-3-propoxypropyl)ethylene diamine, N-(2-hydroxy-2-propoxypropyl)-propylene diamine, N-(2-hydroxy-3-propoxypropyl)-isopropylene diamine, N'-(2-hydroxy-3-propoxypropyl)-isopropylene diamine, N-(2-hydroxy-3-propoxypropyl)-dimethylene triamine, N-(2-hydroxy-3-isopropoxypropyl)-ethylene diamine, N-(2-hydroxy-3-isopropoxypropyl)-propylene diamine, N-(2-hydroxy-3-isopropoxypropyl)-isopropylene diamine, N'-(2-hydroxy-3-isopropoxypropyl)-isopropylene diamine, N-(2-hydroxy-3-isopropoxypropyl)-1,2-dimethylethylene diamine, N-(2-hydroxy-3-isopropoxypropyl)-1,1-dimethylethylene diamine, N'-(2-hydroxy-3-isopropoxypropyl)-1,1-dimethylethylene diamine, N-(2-hydroxy-3-butoxypropyl)-ethylene diamine, N-(2-hydroxy-3-butoxypropyl)-propylene diamine, N-(2-hydroxy-3-butoxypropyl)isopropylene diamine, N'-(2-hydroxy-3-butoxypropyl)isopropylene diamine, N-(2-hydroxy-3-pentoxypropyl)ethylene diamine, N-(2-hydroxy-3-pentoxypropyl)-propylene diamine, N-(2-hydroxy-3-hexylpropyl)-ethylene diamine, N-(2-hydroxy-3-octyloxypropyl)-ethylene diamine, N-(2-hydroxy-3-decyloxypropyl)-ethylene diamine, N-(2-hydroxy-3-dodecyloxypropyl)-ethylene diamine, N-(2-hydroxy-3-dodecyloxypropyl)-isopropylene diamine, N'-(2-hydroxy-3-dodecyloxypropyl)-isopropylene diamine, N-(2-hydroxy-3-tetradecyloxypropyl)-ethylene diamine, N-(2-hydroxy-3-hexadecyloxypropyl)-ethylene diamine, N-(2-hydroxy-3-octadecyloxypropyl)-ethylene diamine, N-(2-hydroxy-3-aryloxypropyl)-ethylene diamine, N-(2-hydroxy-3-aryloxypropyl)-propylene diamine, N-(2-hydroxy-3-aryloxypropyl)isopropylene diamine, N'-(2-hydroxy-3-aryloxypropyl)-isopropylene diamine, N-(2-hydroxy-3-aryloxypropyl)-diethylene triamine, N-(2-hydroxy-3-phenoxypropyl)-ethylene diamine, N-(2-hydroxy-3-phenoxypropyl)-propylene diamine, N-(2-hydroxy-3-phenoxypropyl)-1,2-dimethylethylene diamine, N-(2-hydroxy-3-parachlorophenoxypropyl)-ethylene diamine, N-(2-hydroxy-3-parachlorophenoxypropyl)-1,2-dimethylethylene diamine, N-(2-hydroxy-3-paratrioxypropyl)ethylene diamine, N-(2-hydroxy-3-paratrioxypropyl)propylene diamine, N-(2-hydroxy-3,3,3-trichloropropyl)ethylene diamine, N-(2-hydroxy-2-phenylethyl)-ethylene diamine, N-(2-hydroxy-2-phenylethyl)-isopropylene diamine, N'-(2-hydroxy-2-phenylethyl)-isopropylene diamine, N-(2-hydroxy-2-phenylethyl)-diethylene triamine, N-(2-hydroxy-3-aryloxypropyl)ethylene diamine, N-(2-hydroxy-3-aryloxypropyl)-isopropylene diamine, N'-(2-hydroxy-3-aryloxypropyl)-isopropylene diamine, N-(2-hydroxy-3-aryloxypropyl)-diethylene triamine, N-(1-methyl-2-hydroxy-2-ethoxycarbonylethyl)-ethylene diamine, N-(1-methyl-2-hydroxy-2-ethoxycarbonylethyl)-isopropylene diamine, N-(1-methyl-2-hydroxy-2-ethoxycarbonylethyl)isopropylene diamine, N-(1-methyl-2-hydroxy-2-ethoxycarbonylethyl)-diethylene triamine, N-(2-cyanoethyl)ethylene diamine, N-(2-cyanoethyl)-propylene diamine, N-(2-cyanoethyl)-isopropylene diamine, N'-(2-cyanoethyl)isopropylene diamine, N-(2-cyanoethyl)-diethylene triamine, N-(2-cyanopropyl-ethylene diamine, N-(2-cyanopropyl)-propylene diamine, N(2-cyanoethyl)-isopropylene diamine, N-(aminocarbonylethyl)-ethylene diamine, N-(2-aminocarbonylethyl)-propylene diamine, N-(2-aminocarbonylethyl)-isopropylene diamine, N'-(2-aminocarbonylethyl)-isopropylene diamine, N-(aminocarbonylethyl)-diethylene triamine, N-[2-(2-hydroxyethoxy)-carbonylethyl]-ethylene diamine, N-[2-(2-dimethylaminoethoxy)-carbonylethyl]-ethylene diamine and N-(2-aryloxycarbonylpropyl)-propylene diamine.

Although these polyamines may be manufactured by various methods, they can easily be manufactured by the method described below. For example, they are easily produced by subjecting polyamines (such as alkylene diamines and polyalkylene polyamines) to an addition reaction with acrylic acid derivatives, methacrylic acid derivatives, alkylene sulfides, alkylene oxides, etc. This addition reaction is accomplished by introducing such latter compound dropwise into a given polyamine per se, into an aqueous solution of the polyamine or into an inert solvent containing the polyamine at temperatures within the range of from 0° to 100° C., preferably from 20° to 60° C. Generally, the reaction is exothermic. The evolution of heat in this reaction can easily be controlled by adjusting the speed of dropwise addition of the reactant or by cooling the reaction solution. The polyamine produced can easily be purified by distillation under a vacuum, for example. Where the reaction produces two or more polyamines, they can be separated by purification. Optionally, the two or more polyamines produced simultaneously can be used in their unseparated form as the raw material. Desired polyamines can otherwise be easily produced by subjecting corresponding polyamines to a substitution reaction using halogenated benzyl derivatives and halogenated alkyls. This reaction is readily carried out by introducing such halogenated alkyl derivative dropwise into the given polyamine at temperatures within the range of from 0° to 100° C., preferably from 20° to 60° C. From the reaction solution, the polyamine aimed at is produced by treating the solution with an equivalent weight of an alkali to neutralize the by-produced halogenated hydracid and subjecting the solution to a treatment for purification. This reaction is generally carried out in the presence of an excess of polyamine. A polyamine having two or more identical substituents introduced therein can be produced by adjusting the amount of the polyamine used in the reaction.

Then, the water-soluble N-substituted alkylenebisdithiocarbamate is obtained by causing the polyamine to react with carbon disulfide in an alcohol, DMF or some other suitable solvent and thereafter neutralizing the resultant reaction solution.

The metal salt of the N-substituted alkylenebisdithiocarbamic acid is easily produced by subjecting this water-soluble N-substituted alkylenebisdithiocarbamate to double decomposition with a water-soluble metal salt.

Methods usable for the manufacture of these metal salts of N-substituted alkylenebisdithiocarbamic acids will be described in further detail. Various methods are available. For example, the manufacture may be effected by preparing a solution of the water-soluble salt of a given polydithiocarbamic acid represented by the aforementioned formula and adding to this solution a water-soluble metal salt capable of inducing double decomposition and allowing the reaction to proceed to its completion thereby causing eduction of a precipitate. It may otherwise be effected by adding the two compounds at the same time into a reaction tank or even reversing the sequence of addition of the two compounds. As concerns the solvent, although the reactants are generally used in the form of aqueous solutions, any solvent may be effectively used insofar as solubility of the solutes involved is offered. Examples of the solvent advantageously used for the reaction include water, pyridine, methanol, ethanol, isopropyl alcohol, N-methyl-2-pyrrolidone, sulforan, dimethyl formamide, dimethylacetamide, dimethyl sulfoxide, hexamethylphosphoramide, dioxane, acetone and tetrahydrofuran. These solvents may be used in the form of a mixture of two or more members. The reaction is carried out at temperatures within the range of from 0° to 70° C. The metal salt of polydithiocarbonic acid produced by this reaction is isolated generally in the form of a solid. This fact holds good even when the reaction solution contains water of crystallization and/or a solvent. The by-produced inorganic salts can easily be removed by washing the reaction solution with water after the solvent has been expelled. Where the presence of such inorganic salts has no practical harm, the treatment may be omitted. Examples of the soluble metal salt used for the double decomposition include salts of zinc, manganese, iron, copper, nickel, tin, cobalt, calcium and magnesium. These metal salts are quite effective when they are used in the form of a mixture of two or more members. Specifically, the metal salts are zinc chloride, zinc sulfate, zinc nitrate, zinc acetate, manganese chloride, manganese sulfate, manganese nitrate, manganese acetate, copper chloride, copper sulfate, copper nitrate, copper acetate, iron chloride, iron sulfate, iron nitrate, iron acetate, nickel chloride, nickel sulfate, tin chloride, tin sulfate, tin nitrate, cobalt chloride, cobalt sulfate, cobalt nitrate, calcium chloride, calcium oxide, calcium nitrate, magnesium chloride, magnesium nitrate, and the like. The specific compounds referred to in the foregoing description of the reaction involving the polyamine and the water-soluble metal salt have been cited solely for the purpose of illustration of this invention. Thus, the present invention is not limited to these compounds.

The N-substituted alkylenebisdithiocarbamates of the present invention are generally stable at room temperature. They nevertheless tend to undergo gradual decomposition when exposed to high temperatures or stored for a long time. Incorporation of a stabilizer imparts enhanced stability to these products.

The stabilizer may be added either in the course of manufacture of the salts or during the formulation of pesticidal compositions. Examples of the stabilizer effectively used for this purpose include urea, paraformaldehyde, hexamethylene tetramine, O-tolyl biguanide, diphenyl guanidine, diamino toluene, 1,8-3,6-diendomethylene-1,3,6-8-tetraazacyclodecane, N,N'-dimethyrol urea, 1,3,5-tris(cyanomethyl)-hexanhydrotriazine, N-methyl urea and N,N'-dimethyl urea.

When the N-substituted alkylenebisdithiocarbamate is adopted for agronomic uses, it generally produces no toxic effect but exhibits high control activity. In applications to such uses, although the chemical product of this invention can be used directly in its unmodified form, it may optionally be prepared in any of the known forms such as aqueous solution, dust, wettable powder, granules, emulsion, flow dust, tablets, oil suspension, aqueous suspension, foam and fumigant by use of suitable carriers such as liquid carrier, solid carrier and emulsified dispersant. Examples of the carrier usable advantageously for the formulation include water, alcohols, benzene, xylene, toluene, alkyl naphthalenes, cyclohexane, paraffins, ethers, esters, acetone, methylethyl ketone, methylisobutyl ketone, kerosene, Freon, clay, talc, kaolin, bentonite, acid clay, diatomaceous earth, calcium carbonate, white carbon, quartz alumina, methyl cellulose, starch, gum arabic, polyvinyl alcohol and polyvinyl acetate. Adjuvants generally used for the purpose of formulation of pesticides are also usable. For example, surface active agents such as soap, higher alcohols, sulfates, alkyl-sulfonates, alkylallyl-sulfonates, quarternary ammonium salts, polyalkylene oxide and lignyl sulfonates may be suitably incorporated as extender, emulsifier or dispersant.

The products of this invention can be used in combination with other fungicides, insecticides, miticides, herbicides and plant growth regulators.

When the compound is used in coats of paint in industrial facilities, it protects such facilities against otherwise possible pollution and damage done by mildew and other microorganisms and also against pollution done by slime and algae.

Now, the present invention will be described in detail with reference to working examples. It should be noted that the present invention is not limited in any way to these examples.

EXAMPLE 1

In 200 ml of water, 47 g (0.05 mol) of an aqueous 40% sodium N-(2-hydroxy-3-isopropoxypropyl)-ethylenebisdithiocarbamate was stirred at room temperature. To the resultant aqueous solution, 13.6 g (0.05 mol) of an aqueous 50% zinc chloride solution was gradually added dropwise. After the dropwise addition, the reaction solution was stirred continuously for three hours at room temperature. The crystals which consequently educed in the solution were separated by filtration and washed with water. The washed crystals were dried at 50° to 60° C. under a vacuum. Thus was obtained zinc N-(2-hydroxy-3-isopropoxypropyl)-ethylenebisdithiocarbamate (Compound No. 6). Copper, iron, nickel, cobalt, tin, calcium or magnesium salt could easily be produced by using the water-soluble salt of copper, iron, nickel, cobalt, tin, calcium, or magnesium in the equivalent weight in place of zinc chloride. The compounds prepared by the procedure described above were as shown below.

| Compound No. | Structural formula of compound | Appearance |
| --- | --- | --- |
| 1 | $Zn_{/2}-S-C(=S)-N(H)-CH_2CH_2-N(CH_2CH(OH)CH_2OH)-C(=S)-S-Zn_{/2}$ | Yellow powdery solid |
| 2 | $Zn_{/2}-S-C(=S)-N(H)-CH_2CH_2-N(CH_2CH(OH)CH_2-O-CH_3)-C(=S)-S-Zn_{/2}$ | White powdery solid |
| 3 | $Cu_{/2}-S-C(=S)-N(H)-CH_2CH_2-N(CH_2CH(OH)CH_2-O-CH_3)-C(=S)-S-Cu_{/2}$ | Black powdery solid |
| 4 | $Fe_{/3}-S-C(=S)-N(H)-CH_2CH_2-N(CH_2CH(OH)CH_2-O-CH_3)-C(=S)-S-Fe_{/3}$ | Blackish brown powdery solid |
| 5 | $Zn_{/2}-S-C(=S)-N(H)-CH_2CH_2-N(CH_2CH(OH)CH_2-O-C_2H_5)-C(=S)-S-Zn_{/2}$ | Light yellow powdery solid |
| 6 | $Zn_{/2}-S-C(=S)-N(H)-CH_2CH_2-N(CH_2CH(OH)CH_2-O-CH(CH_3)_2)-C(=S)-S-Zn_{/2}$ | White powdery solid |

-continued

| Compound No. | Structural formula of compound | Appearance |
|---|---|---|
| 7 | $Zn_{/2}-S-\underset{\underset{S}{\|}}{C}-\underset{H}{N}\diagdown\diagup\underset{}{N}-\underset{\underset{S}{\|}}{C}-S-Zn_{/2}$ with substituent $CH_2\overset{OH}{\underset{\|}{C}H}CH_2-O-C_4H_9(n)$ | White powdery solid |
| 8 | same core with $CH_2\overset{OH}{\underset{\|}{C}H}CH_2-O-CH\diagup\diagdown\genfrac{}{}{0pt}{}{C_2H_5}{C_6H_{13}}$ | White powdery solid |
| 9 | same core with $CH_2\overset{OH}{\underset{\|}{C}H}CH_2-O-CH_2CH=CH_2$ | White powdery solid |
| 10 | same core with $CH_2\overset{OH}{\underset{\|}{C}H}CH_2-O-\text{C}_6H_5$ | White powdery solid |
| 11 | same core with $CH_2\overset{OH}{\underset{\|}{C}H}CH_2-O-\text{C}_6H_4-CH_3$ | White powdery solid |
| 12 | core with $CH_3$ branch and $CH_2\overset{OH}{\underset{\|}{C}H}CH_2-O-CH\diagup\diagdown\genfrac{}{}{0pt}{}{CH_3}{CH_3}$ | Yellow powdery solid |
| 13 | core with $CH_3{}^*$ branch and $CH_2\overset{OH}{\underset{\|}{C}H}CH_2-O-CH_3$ | Light yellow powdery solid |
| 14 | $Zn_{/2}-S-\underset{\underset{S}{\|}}{C}-\underset{H}{N}\diagdown\diagup\underset{}{N}-\underset{\underset{S}{\|}}{C}-S-Zn_{/2}$ with $CH_2COOC_2H_5$ | Yellow powdery solid |
| 15 | Zn core with $CH_2CH_2COOCH_3$ | White powdery solid |
| 16 | Cu core with $CH_2CH_2COOCH_3$ | Brown powdery solid |
| 17 | Fe core with $CH_2CH_2COOCH_3$ | Blackish Brown powdery solid |
| 18 | Zn core with $CH_2CH_2COOC_2H_5$ | White powdery solid |
| 19 | Cu core with $CH_2CH_2COOC_2H_5$ | Brown powdery solid |
| 20 | Fe core with $CH_2CH_2COOC_2H_5$ | Black powdery solid |

-continued

| Compound No. | Structural formula of compound | Appearance |
|---|---|---|
| 21 | Ni—S—C(=S)—N(H)—CH₂CH₂—N(CH₂CH₂COOC₂H₅)—C(=S)—S—Ni | Blackish brown powdery solid |
| 22 | Zn/₂—S—C(=S)—N(H)—CH₂CH₂—N(CH₂CH₂COOC₄H₉(iso))—C(=S)—S—Zn/₂ | White powdery solid |
| 23 | Zn/₂—S—C(=S)—N(H)—CH₂CH(CH₃)—N(CH₂CH₂COOCH₂CH₂—OH)—C(=S)—S—Zn/₂ | Light yellow powdery solid |
| 24 | Zn/₂—S—C(=S)—N(H)—CH₂CH₂—N(CH₂CH(CH₃)—COOCH₃)—C(=S)—S—Zn/₂ | Light yellow powdery solid |
| 25 | Zn/₂—S—C(=S)—N(H)—CH₂CH₂—N(CH₂CH(CH₃)—COOC₂H₅)—C(=S)—S—Zn/₂ | Light yellow powdery solid |
| 26 | Zn/₂—S—C(=S)—N(H)—CH₂CH₂—N(CH₂CH(CH₃)COOCH(CH₃)₂)—C(=S)—S—Zn/₂ | Light yellow powdery solid |
| 27 | Zn/₂—S—C(=S)—N(H)—CH₂CH₂—N(CH₂CH(CH₃)COOCH(CH₃)(C₂H₅))—C(=S)—S—Zn/₂ | White powdery solid |
| 28 | Zn/₂—S—C(=S)—N(H)—CH₂CH₂—N(CH₂CH(CH₃)COO—C(CH₃)₃)—C(=S)—S—Zn/₂ | Light yellow powdery solid |
| 29 | Zn/₂—S—C(=S)—N(H)—CH₂CH₂—N(CH₂CH(CH₃)COOC₁₂H₂₅(n))—C(=S)—S—Zn/₂ | Light yellow powdery solid |
| 30 | Zn/₂—S—C(=S)—N(H)—CH₂CH₂—N(CH(CH₃)—CH(OH)COOC₂H₅)—C(=S)—S—Zn/₂ | Light yellow powdery solid |
| 31 | Zn/₂—S—C(=S)—N(H)—CH₂CH(CH₃)—N(CH₂CH(CH₃)COOCH(CH₃)₂)—C(=S)—S—Zn/₂ | Light Yellow powdery solid |
| 32 | Zn/₂—S—C(=S)—N(H)—CH(CH₃)CH(CH₃)—N(CH₂CH(CH₃)COOCH(CH₃)₂)—C(=S)—S—Zn/₂ | Light Yellow powdery solid |
| 33 | Zn/₂—S—C(=S)—N(H)—CH₂CH₂—N(CH₂CH₂—C≡N)—C(=S)—S—Zn/₂ | White powdery solid |

-continued

| Compound No. | Structural formula of compound | Appearance |
|---|---|---|
| 34 | Zn/2—S—C(=S)—N(H)—CH(CH3)—N(CH2—CH(CH3)COOCH2CH2N(CH3)CH3)—C(=S)—S—Zn/2 | White powdery solid |
| 35 | Zn/2—S—C(=S)—N(H)—CH(CH3)—N(CH2—CH(CH3)COOCH2—CH=CH2)—C(=S)—S—Zn/2 | Yellow powdery solid |
| 36 | Zn/2—S—C(=S)—N(H)—CH2CH2—N(CH2CH2SH)—C(=S)—S—Zn/2 | Light yellow powdery solid |
| 37 | Cu/2—S—C(=S)—N(H)—CH2CH2—N(CH2CH2SH)—C(=S)—S—Cu/2 | Blackish brown powdery solid |
| 38 | Fe/3—S—C(=S)—N(H)—CH2CH2—N(CH2CH2SH)—C(=S)—S—Fe/3 | Black powdery solid |
| 39 | Zn/2—S—C(=S)—N(H)—CH2CH2—N(CH2CH(CH3)—SH)—C(=S)—S—Zn/2 | Yellow powdery solid |
| 40 | Zn/2—S—C(=S)—N(H)—CH(CH3)—N(CH2CH2SH)—C(=S)—S—Zn/2 | Yellow powdery solid |
| 41 | Zn/2—S—C(=S)—N(H)—CH2CH2—N(C8H17)—C(=S)—S—Zn/2 | Yellow powdery solid |
| 42 | Zn/2—S—C(=S)—N(H)—CH2CH2—N(C10H21)—C(=S)—S—Zn/2 | Yellow powdery solid |
| 43 | Zn/2—S—C(=S)—N(H)—CH2CH2—N(C12H25)—C(=S)—S—Zn/2 | Yellow powdery solid |
| 44 | Cu/2—S—C(=S)—N(H)—CH2CH2—N(C12H25)—C(=S)—S—Cu/2 | Black powdery solid |
| 45 | Ca/2—S—C(=S)—N(H)—CH2CH2—N(C12H25)—C(=S)—S—Ca/2 | Yellow powdery solid |
| 46 | Mg/2—S—C(=S)—N(H)—CH2CH2—N(C12H25)—C(=S)—S—Mg/2 | Light yellow powdery solid |
| 47 | Fe/3—S—C(=S)—N(H)—CH2CH2—N(C12H25)—C(=S)—S—Fe/3 | Black powdery solid |
| 48 | Ni/2—S—C(=S)—N(H)—CH2CH2—N(C12H25)—C(=S)—S—Ni/2 | Black powdery solid |
| 49 | Co/3—S—C(=S)—N(H)—CH2CH2—N(C12H25)—C(=S)—S—Co/3 | Black powdery solid |

-continued

| Compound No. | Structural formula of compound | Appearance |
|---|---|---|
| 50 | Zn/2—S—C(=S)—N(H)—CH₂CH₂—N(C₁₄H₂₉)—C(=S)—S—Zn/2 | Yellow powdery solid |
| 51 | Zn/2—S—C(=S)—N(H)—CH₂CH₂—N(C₁₆H₃₃)—C(=S)—S—Zn/2 | Yellowish Orange powdery solid |
| 52 | Zn/2—S—C(=S)—N(H)—CH₂CH₂—N(C₁₈H₃₇)—C(=S)—S—Zn/2 | Light Yellow powdery solid |
| 53 | Zn/2—S—C(=S)—N(H)—CH₂CH₂—N(CH₂—C₆H₄—CH₃)—C(=S)—S—Zn/2 | Light Yellow powdery solid |
| 54 | Zn/2—S—C(=S)—N(H)—CH₂CH₂—N(CH₂—(2,4-(CH₃)₂C₆H₃))—C(=S)—S—Zn/2 | Yellow powdery solid |
| 55 | Zn/2—S—C(=S)—N(H)—CH₂CH₂—N(CH₂—(3,4-(CH₃)₂C₆H₃))—C(=S)—S—Zn/2 | Light yellow powdery solid |
| 56 | Zn/2—S—C(=S)—N(H)—CH₂CH₂—N(CH₂—(2,4,5-(CH₃)₃C₆H₂))—C(=S)—S—Zn/2 | Yellow powdery solid |
| 57 | Zn/2—S—C(=S)—N(H)—CH₂CH₂—N(CH₂—C₆H₄—Cl)—C(=S)—S—Zn/2 | Yellow powdery solid |
| 58 | Zn/2—S—C(=S)—N(H)—CH₂CH₂—N(CH₂—C₆H₄—C₁₂H₂₅)—C(=S)—S—Zn/2 | Yellowish orange powdery solid |
| 59 | H₂NCH₂CH₂ group; Zn/2—S—C(=S)—N—CH₂CH₂—N(CH₂—(2,4,5-(CH₃)₃C₆H₂))—C(=S)—S—Zn/2 | Yellow powdery solid |
| 60 | Zn/2—S—C(=S)—N(H)—CH₂CH₂—N(CH₂CH(OH)—C₆H₅)—C(=S)—S—Zn/2 | White powdery solid |

*designates question of methyl group on ethylene chain not determined

EXAMPLE 2

In 50 ml of water, 13 g (0.02 mole) of an aqueous 48% sodium N-(2-mercaptoethyl)-ethylenebisdithiocarbamate was stirred at 45° to 50° C. The remaining part of the procedure was performed under a current of nitrogen gas. To the resultant sodium salt solution, 9.5 g (0.02 mole) of an aqueous 26.5% manganous chloride solution was gradually added dropwise at temperatures of 40° to 50° C. After the dropwise introduction, the resultant mixture was stirred at 45° C. for one hour. The crystals which consequently educed in the solution were separated by filtration and washed with water. The washed crystals were dried under a vacuum to produce manganese N-(2-mercaptoethyl)-ethylenebisdithiocarbamate (61). The compounds produced by this procedure were as follows:

| Compound No. | Structural formula of compound | Appearance |
| --- | --- | --- |
| 61 | $Mn_{1/2}-S-C(=S)-N(H)-CH_2CH_2-N-C(=S)-S-Mn/2$ with $CH_2CH_2SH$ branch | Yellow powdery solid |
| 62 | $M_{n/2}-S-C(=S)-N(H)-CH_2CH_2-N-C(=S)-S-M_{n/2}$ with $CH_2CH_2-O-C(=S)-S-M_{n/2}$ branch | Yellowish orange powdery solid |

EXAMPLE 3

In 300 ml of water, 24 g (0.03 mole) of an aqueous 50% sodium N-(2-sodiumxanthogenylethyl)-ethylenebisdithiocarbamate solution was stirred at room temperature. To the resultant sodium salt solution, 13 g (0.045 mole) of an aqueous 50% zinc chloride solution was gradually added dropwise at room temperature. After the dropwise addition, the resultant mixture was stirred at 45° C. for one hour. The crystals which consequently were educed were separated by filtration and washed with water. The washed crystals were dried at 50° to 60° C. under a vacuum (63). A copper salt or iron salt could be easily obtained by using an equivalent weight of a water-soluble salt of copper or iron in place of zinc chloride. The compounds obtained by this procedure were as shown below.

| Compound No. | Structural formula of compound | Appearance |
| --- | --- | --- |
| 63 | $Zn/2-S-C(=S)-N(H)-\cdots-N-C(=S)-S-Zn/2$ with $CH_2CH_2-O-C(=S)-S-Zn/2$ branch | Yellow powdery solid |
| 64 | $Fe/3-S-C(=S)-N(H)-\cdots-N-C(=S)-S-Fe/3$ with $CH_2CH_2-O-C(=S)-S-Fe/3$ branch | Black powdery solid |
| 65 | $Zn/2-S-C(=S)-N(H)-\cdots-N(CH_3)-C(=S)-S-Zn/2$ with $CH_2CH_2-O-C(=S)-S-Zn/2$ branch | Yellow powdery solid |
| 66 | $Zn/2-S-C(=S)-N(H)-\cdots-N-C(=S)-S-Zn/2$ with $CH_2CH(CH_3)-O-C(=S)-S-Zn/2$ branch | Yellow powdery solid |
| 67 | $Zn/2-S-C(=S)-N(H)-\cdots-N(CH_3)-C(=S)-S-Zn/2$ with $CH_2CH(CH_3)-O-C(=S)-S-Zn/2$ branch | Yellowish orange powdery solid |

TEXT 1

To cucumbers (species: Tokiwa-hikari Sango) grown in a Firon house at the age of three-leaf stage, a given metal salt diluted to a prescribed concentration was applied with the aid of a small glass spray (with an extender incorporated in the diluted solution). On the seonc day after this spraying, a suspension of spores of scab (*Cladosporium cucumerinum*) was sprayed on the treated cucumbers. The cucumbers were kept in a hot house with humidity of not less than 90% to promote the infection of cucumbers by the disease germ. On the 10th day after this inoculation of the spores, the two uppermost of the leaves which were open at the time of the spraying were examined and rated for degree of disease (on the 0-4 scale) to calculate the control index. The metal salt was prepared in the form of 75% wettable powder.

| Test for Control of Scab Disease on Cucumbers | | |
|---|---|---|
| Compound No. | Concentration of essential component (ppm) | Control Index |
| 1 | 1500 | 74 |
| 2 | " | 72 |
| 3 | " | 70 |
| 4 | " | 76 |
| 5 | " | 68 |
| 6 | " | 89 |
| 7 | " | 65 |
| 8 | " | 81 |
| 9 | " | 73 |
| 10 | " | 80 |
| 11 | " | 72 |
| 12 | " | 88 |
| 13 | " | 86 |
| 14 | " | 78 |
| 15 | " | 65 |
| 16 | " | 82 |
| 17 | " | 79 |
| 18 | " | 70 |
| 19 | " | 61 |
| 20 | " | 76 |
| 21 | " | 78 |
| 22 | " | 64 |
| 23 | " | 78 |
| 24 | " | 65 |
| 25 | " | 77 |
| 26 | " | 82 |
| 27 | " | 66 |
| 28 | " | 82 |
| 29 | " | 78 |
| 30 | " | 72 |
| 31 | " | 83 |
| 32 | " | 79 |
| 33 | " | 70 |
| 34 | " | 74 |
| 35 | " | 68 |
| 36 | " | 82 |
| 37 | " | 72 |
| 38 | " | 80 |
| 39 | " | 75 |
| 40 | " | 86 |
| 41 | " | 70 |
| 42 | " | 69 |
| 43 | " | 75 |
| 44 | " | 64 |
| 45 | " | 77 |
| 46 | " | 78 |
| 47 | " | 79 |
| 48 | " | 73 |
| 49 | " | 70 |
| 50 | " | 60 |
| 51 | " | 73 |
| 52 | " | 72 |
| 53 | " | 65 |
| 54 | " | 81 |
| 55 | " | 75 |
| 56 | " | 58 |
| 57 | " | 75 |
| 58 | " | 71 |
| 59 | " | 66 |
| 60 | " | 82 |
| 61 | " | 76 |
| 62 | " | 73 |
| 63 | " | 70 |
| 64 | " | 79 |
| 65 | " | 79 |
| 66 | " | 69 |
| 67 | " | 80 |
| No treatment | — | 0 |

TEST 2

To tomatoes (species: Sarashina-Fukuju) grown in a Firon house at the age of seven-leaf stage, a given metal salt diluted to a prescribed concentration was applied with the aid of a small powered spray (with an extender incorporated in the diluted solution). On the second day after this spraying, a suspension of spores of disease germ was sprayed uniformly on the treated tomatoes by way of innoculation. On the 10th day after this innoculation, five main leaves per stock and seven small leaves per main leaf were examined to take count of disease spots (on the scale of 0, 1 and 2) to calculate the control index. The metal salt was prepared in the form of 75% wettable powder.

| Test for Control of Scab Disease on Tomatoes | | | |
|---|---|---|---|
| Compound No. | Concentration of essential component (ppm) | Control Index | Phyto-toxicity |
| 1 | 1500 | 74 | — |
| 2 | " | 81 | — |
| 6 | " | 86 | — |
| 12 | " | 73 | — |
| 20 | " | 69 | — |
| 21 | " | 75 | — |
| 26 | " | 84 | — |
| 30 | " | 77 | — |
| 33 | " | 79 | — |
| 36 | " | 80 | — |
| 39 | " | 68 | — |
| 44 | " | 77 | — |
| 46 | " | 76 | — |
| 53 | " | 83 | — |
| 59 | " | 79 | — |
| 61 | " | 75 | — |
| 62 | " | 85 | — |
| 67 | " | 76 | — |
| No Treatment | — | 0 | — |

We claim:

1. A metal salt of N-substituted alkylenebisdithiocarbamic acid represented by the general formula:

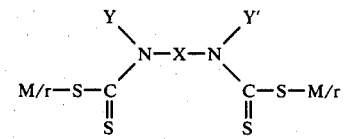

wherein, X denotes a straight or branched aliphatic chain containing at least two carbon atoms linking the nitrogen atoms, Y and Y' each denote a hydrogen atom (excluding the case wherein both Y and Y' are a hydrogen atom),

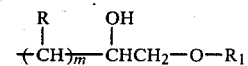

(where, R is a hydrogen atom or an alkyl group, $R_1$ is a hydrogen atom, an alkyl group, an unsaturated alkyl group, a phenyl group, or a phenyl group substituted with lower alkyl groups or one or more halogen atoms, and m is an integer having the value of 0, 1 or 2),

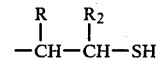

(where R and $R_2$ are the same as described above),

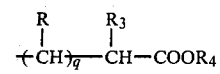

(R is the same as described above, $R_3$ is a hydrogen atom, a lower alkyl group or a hydroxyl group, $R_4$ is an alkyl group, a dialkylaminoalkyl group, an unsaturated alkyl group, a hydroxyalkyl group or a salt, and q is an integer having the value of 0 or 1), $$\begin{array}{cc} R & R_3 \\ | & | \\ \text{+CH+}_q\text{—CH—NH}_3 \end{array}$$

(R, R$_3$ and q are the same as described above), $$\begin{array}{cc} R & R_3 \\ | & | \\ \text{+CH+}_m\text{—CH—O—C—S—M/r} \\ & \quad \| \\ & \quad S \end{array}$$

(where, R, R$_3$ and m are the same as described above, and M and r are the same as described herein below), or $$\begin{array}{cc} R & OH & R_3 \\ | & | & \\ \text{+CH+}_m\text{—CH—} \bigcirc \end{array}$$

(where, R, R$_3$ and m are the same as described above), M denotes a member of the group consisting of zinc, copper, iron, nickel, magnesium, calcium, cobalt, manganese and tin, and r denotes a valency.

2. A metal salt according to claim 1 having the formula:

$$\begin{array}{c} \text{H} \qquad\qquad \text{OH} \\ \quad\backslash \qquad\qquad | \\ \quad\text{N—CH}_2\text{CH}_2\text{N} \\ \text{M/r—S—C} \qquad\qquad \text{C—S—M/r} \\ \quad \| \qquad\qquad\qquad \| \\ \quad S \qquad\qquad\qquad S \end{array}$$

wherein R$^1$ is an isopropyl, a 3-nonyl or a phenyl group.

3. A metal salt according to claim 1 having the formula:

$$\begin{array}{c} \text{H} \quad \text{CH}_3 \quad \text{OH} \\ \backslash \quad | \quad\quad\quad | \\ \text{N—CHCH}_2\text{N—CH}_2\text{CHCH}_2\text{OR}_1 \\ \text{M/r—S—C} \quad\quad\quad \text{C—S—M/r} \\ \| \quad\quad\quad\quad \| \\ S \quad\quad\quad\quad S \end{array}$$

wherein R$^1$ is an isopropyl, or a methyl group.

4. A metal salt according to claim 1 having the formula:

$$\begin{array}{c} \text{CH}_3 \\ \text{H} \quad\quad\quad | \\ \backslash \quad\quad\quad \text{CH}_2\text{CHCO}_2\text{R}_1 \\ \text{N—CH}_2\text{CH}_2\text{N} \\ \text{M/r—S—C} \quad\quad \text{C—S—M/r} \\ \| \quad\quad\quad \| \\ S \quad\quad\quad S \end{array}$$

wherein R$^1$ is an isopropyl, or butyl group.

5. A metal salt according to claim 1 having the formula:

$$\begin{array}{c} \text{CH}_3 \\ \text{H} \quad \text{CH}_3 \quad \text{CH}_2\text{CHCO}_2\text{R}_1 \\ \backslash \quad | \quad\quad / \\ \text{N—CH}_2\text{CHCH}_2\text{N} \\ \text{M/r—S—C} \quad\quad \text{C—S—M/r} \\ \| \quad\quad \| \\ S \quad\quad S \end{array}$$

wherein R$^1$ is an isopropyl group.

6. A metal salt according to claim 1 having the formula:

$$\begin{array}{c} \text{H} \quad\quad\quad \text{CH}_2\text{CH}_2\text{SH} \\ \backslash \quad\quad\quad / \\ \text{NCH}_2\text{CH}_2\text{N} \\ \text{M/r—S—C} \quad\quad \text{C—S—M/r.} \\ \| \quad\quad \| \\ S \quad\quad S \end{array}$$

7. A metal salt according to claim 1 having the formula:

$$\begin{array}{c} \text{H} \quad \text{CH}_3 \quad \text{CH}_2\text{CH}_2\text{SH} \\ \backslash \quad | \quad\quad / \\ \text{NCH}_2\text{CHCH}_2\text{N} \\ \text{M/r—S—C} \quad\quad \text{C—S—M/r.} \\ \| \quad\quad \| \\ S \quad\quad S \end{array}$$

8. A metal salt according to claim 1 having the formula:

$$\begin{array}{c} \text{CH}_3 \\ \text{H} \quad\quad\quad \text{CH}_2\text{—}\bigcirc\text{—CH}_3. \\ \backslash \quad\quad\quad / \\ \text{NCH}_2\text{CH}_2\text{N} \\ \text{M/r—S—C} \quad\quad \text{C—S—M/r} \\ \| \quad\quad \| \\ S \quad\quad S \end{array}$$

9. A metal salt according to claim 1 having the formula:

$$\begin{array}{c} \text{OH} \\ \text{H} \quad\quad\quad | \\ \backslash \quad\quad\quad \text{CH}_2\text{CH—}\bigcirc \\ \text{NCH}_2\text{CH}_2\text{N} \\ \text{M/r—S—C} \quad\quad \text{C—S—M/r} \\ \| \quad\quad \| \\ S \quad\quad S \end{array}$$

10. A metal salt according to claim 1 having the formula:

$$\begin{array}{c} \text{CH}_3 \\ \text{H} \quad \text{CH}_3 \quad \text{CH}_2\text{CH—O—C—M/r.} \\ \backslash \quad | \quad\quad\quad\quad \| \\ \text{NCH}_2\text{CHCH}_2\text{N} \quad\quad S \\ \text{M/r—S—C} \quad\quad \text{C—S—M/r} \\ \| \quad\quad \| \\ S \quad\quad S \end{array}$$

11. A metal salt having the formula:

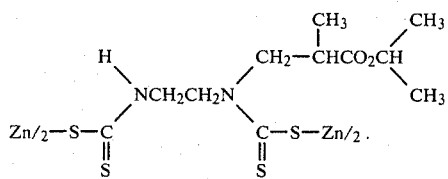
12. An agricultural fungicidal composition which comprises as the active ingredient a fungicidally effective amount of a metal salt according to claim 1, 2, 3, 4, 5, 6, 7, 8, 9, 10 or 11 and an agronomically acceptable carrier.
13. A fungicidal composition which comprises an agronomically acceptable carrier and, as active ingredient, a compound according to claim 1.
* * * * *